US00PP36444P2

(12) United States Plant Patent
Stewart

(10) Patent No.: US PP36,444 P2
(45) Date of Patent: Feb. 11, 2025

(54) ***PHLOX* PLANT NAMED 'Material Girl'**

(50) Latin Name: *Phlox paniculata*
Varietal Denomination: Material Girl

(71) Applicant: Brigitta Stewart, Fowlerville, MI (US)

(72) Inventor: Brigitta Stewart, Fowlerville, MI (US)

( * ) Notice: Subject to any disclaimer, the term of this patent is extended or adjusted under 35 U.S.C. 154(b) by 0 days.

(21) Appl. No.: 18/445,776

(22) Filed: Jan. 26, 2024

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 6/70; A01H 5/02
See application file for complete search history.

*Primary Examiner* — Keith O. Robinson

(57) ABSTRACT

A new and unique hybrid cultivar of *Phlox* plant named 'Material Girl' of medium to tall-height, multi-stemmed, upright habit. The foliage is lanceolate, dark-green, with good powdery mildew resistance on stiff stems. The new plant has fragrant fuchsia-purple flowers with slightly darker eyes that are produced on large heads of branched peduncles and nearly cover the top of the plant beginning mid-July and continuing and reblooming for about six weeks through late summer. 'Material Girl' is especially suitable as a potted plant, for the garden, for attracting hummingbirds and butterflies, and for cut flower arrangements.

2 Drawing Sheets

Botanical classification: *Phlox paniculata.*
Variety denomination: 'Material Girl'.

STATEMENT REGARDING PRIOR DISCLOSURES UNDER 37 CFR 1.77(B)(6)

The first offer for sale of *Phlox* 'Material Girl' was on Feb. 2, 2023, and the first sale was by Walters Gardens, Inc. on Jul. 10, 2023, to W. W. Greenhouse. Walters Gardens, Inc. published an advertisement in their "Walters Gardens 23-24 Catalog" on May 19, 2023, and prior to this Walters Gardens, Inc. released a photo and brief description of the new plant on Feb. 1, 2023. Walters Gardens, Inc. obtained the new plant and all information relating thereto, from the inventor. No plants of *Phlox* 'Material Girl' have been sold or offered for sale in this country or anywhere in the world under this or any name, nor has any disclosure of the new plant been made more than one year prior to the filing date of this application and such sale or disclosure within one year was either derived directly or indirectly from the inventor.

BACKGROUND OF THE INVENTION

The present invention relates to a new and distinct hybrid Tall *Phlox* plant known as *Phlox* 'Material Girl' and will be referred to hereafter by its cultivar name or the "new plant". The new plant was the result of a collection of seeds from various garden locations. The seeds were then planted and grown in an isolation bed to test for mildew resistance. The isolation bed was in cultivation at a nursery in Fowlerville, Michigan. Further trials of the seedlings were performed at a nursery in Zeeland, Michigan. During the trial process the new plant arising as a single seedling selection from unknown parentage was identified by the breeder code "Brigitta" before final evaluations and being assigned the cultivar name 'Material Girl'.

'Material Girl' has been asexually propagated by tip and basal stem cuttings in the greenhouses at the same nursery in Zeeland, Michigan since 2012, as well as by shoot tip tissue culture. The unique characteristics of the new plant are reproducible and stable in successive generations of asexually propagated plants with the resultant plants identical to the original selection.

BRIEF SUMMARY OF THE PLANT

*Phlox* 'Material Girl' is unique from its parents and all other Tall Garden *Phlox* or other hybrid *Phlox* known to the inventor. The closest comparison cultivars known to the inventor are: 'Ultraviolet' U.S. Plant Pat. No. 33,607, 'Laura' (not patented), 'Barfourteen' U.S. Plant Pat. No. 12,605, 'Balsukafus' U.S. Plant Pat. No. 33,005, 'Nicky' (not patented), and 'Cover Girl' U.S. Plant Pat. No. 32,323.

'Ultraviolet' is slightly shorter in habit with darker magenta-violet flowers. 'Laura' is more compact in habit and the flower is fuchsia-purple with a white center and dark fuchsia purple eye. 'Barfourteen' has a much shorter habit and the flower petals are a magenta-purple to rose. 'Balsukafus' is much smaller in habit, the inflorescence is much smaller and has fewer flowers, the flower faces are more cupped and less flat, and the flower color is more reddish-purple. 'Nicky' has deeper magenta-colored flowers on smaller heads. 'Cover Girl' flowers are slightly smaller, with more imbricate limbs, and the color is slightly more reddish-purple.

No comparison of either the female or male parents is possible.

'Material Girl' differs from all other *Phlox* known to the inventor in the following repeatedly observed traits in combination:

1. Medium to tall-height plants of upright habit, producing clean, dark-green, lanceolate leaves;
2. Foliage shows good powdery mildew resistance;

3. Multiple stems produce large, branched mounds of flowers starting in mid-July for about six weeks;
4. Fragrant fuchsia-purple flowers with slightly darker eyes on strong stiff stems;
5. Flowers cover nearly the entire top of the plant.

BRIEF DESCRIPTION OF THE DRAWINGS

The photographs of the new plant demonstrate the unique traits and the overall appearance of three-year-old plants of 'Material Girl' grown in a full-sun trial garden in Zeeland, Michigan. The colors are as accurate as reasonably possible with color reproductions. Changes in ambient light spectrum, source, temperature, and direction may cause the appearance of minor color variations.

DETAILED BOTANICAL DESCRIPTION

Figure 1:
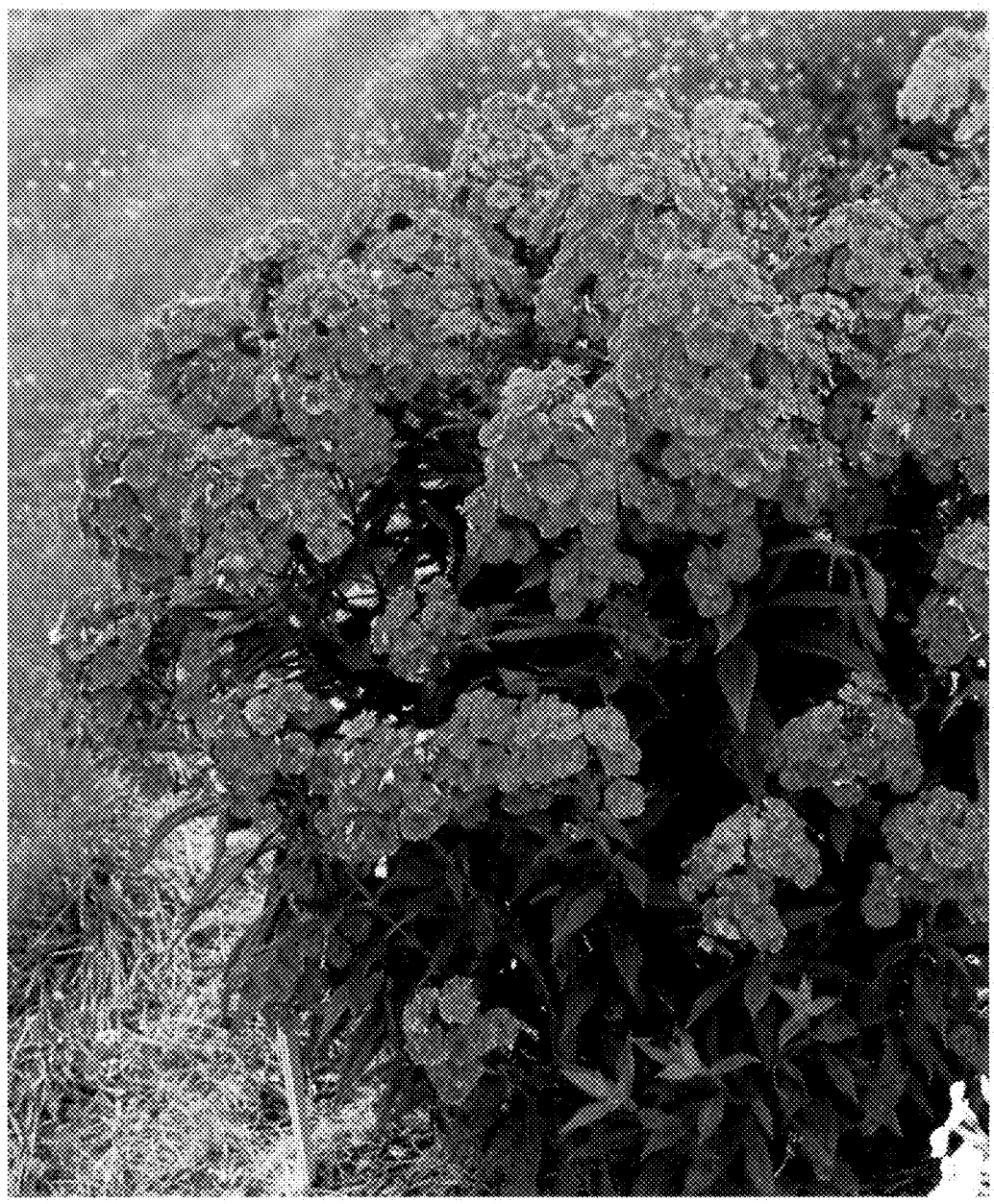
FIG. 1 shows the habit of the new plant in peak flower in the landscape.
Figure 2:
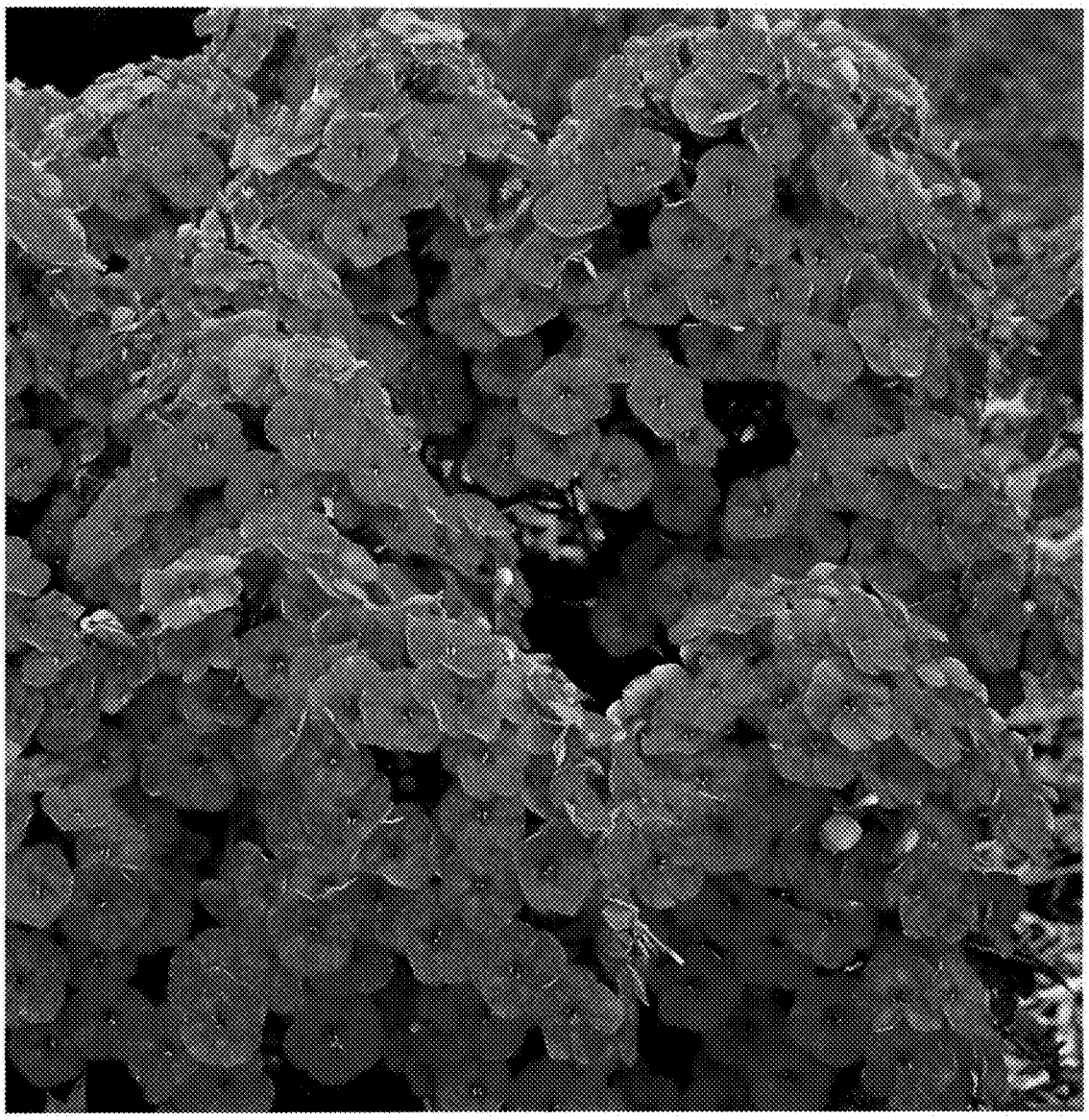
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Material Girl' has not been observed in all possible environments. The phenotype may vary slightly with different growing environments such as temperature, light, fertility, soil pH, moisture, and maturity levels, but without any change in the genotype. The following observations and size descriptions are based on two-year-old plants in a partially-shaded greenhouse and a full-sun trial garden of a wholesale perennial nursery in Zeeland, Michigan with supplemental fertilizer and water as needed.

Botanical classification: *Phlox paniculata;*

Parentage: The female and male parents are unknown;

Plant habit: Hardy herbaceous perennial, densely upright, producing about 8 rigid mostly upright stems; flowering at up to 95 cm tall and about 76 cm wide; flowering begins mid-July in Michigan continuing for about 6 weeks and repeating into late summer;

Propagation: Stem cuttings; rooting in about 21 days;

Time to produce finished crop in 3.8-liter pots: About 10 to 12 weeks from a 25 mm liner; moderate rate of growth;

Root: Primary roots to about 1 mm thick; secondary fibrous and freely branching; color creamy white to tan depending on soil type; color of active roots nearest RHS 159C depending on soil components;

Leaves: Simple; opposite; ovoid; acute apex; rounded to truncate base; sessile; micro-ciliolate margin; tough, coriaceous;

Leaf size: To about 12.8 cm long by about 3.2 cm wide; average about 8.7 cm long by about 2.8 cm wide; becoming smaller distally;

Leaf surfaces: Micro-puberulent and slightly lustrous adaxial, micro-puberulent and matte abaxial;

Leaf color expanding: Adaxial between RHS 143A and RHS 146A, abaxial nearest RHS 147B;

Leaf color at flowering: Adaxial nearest RHS NN137B, abaxial nearest RHS 147B;

Foliage fragrance: None detected;

Veins: Pinnate; glabrous adaxial and abaxial; midrib about 1.5 mm wide at base, slightly sunken adaxial and raised abaxial;

Vein color: Adaxial midrib nearest RHS 146C and lateral veins nearest RHS 146A, abaxial midrib nearest RHS 145C and lateral veins nearest RHS 146A;

Petiole: Leaves sessile;

Stems: About 8 per plant; cylindrical; stiff; wiry; strong; rapidly glabrescent to glabrous; mostly upright; to about 56 cm long below peduncle and 12 mm diameter at base, average about 50 cm long and 9 mm diameter at base;

Stem color: Proximally nearest RHS 146C, distally striated with nearest RHS 199D and RHS 146C;

Nodes: About 15 to 21 per stem below initial flowers plus 9 nodes in branched flower head; average internode length about 2.8 cm below flowers;

Node color: Nearest RHS 146C;

Inflorescence: A branched compound corymb of about 100 flowers; flowering portion to about 20 cm long and 15 cm across;

Flowers: Perfect; salverform with a flat face and long fused tube; actinomorphic; typically with five petals; about 24 mm long total with corolla tube about 22 mm long and 2.5 mm diameter at the base and 4 mm diameter below face; face about 32 mm across; attitude upright to slightly outward; self-cleaning;

Flower longevity: Individually about 5 days on plant or as a cut flower;

Flower fragrance: Lightly sweet;

Buds one to two days prior to opening: Clavate; acute apex with petals convolute; base fused; total bud about 27 mm long, tube about 17 mm long and 2.5 mm diameter in tube base, bulb 15 mm long and swollen to 5 mm diameter toward apex;

Bud color: Petals nearest RHS N81A in bulb, and between RHS N79C and RHS 79B corolla tube;

Petals: Five; sympetalous; margin entire; apex rounded; with obdeltoid limb and base fused into corolla tube; adaxial face and tube glabrous except proximal 5 mm of corolla tube pubescent, abaxial face glabrous and tube puberulent; limbs moderately imbricate, about 20percent over the next petal;

Petal size: Limb to about 17 mm wide and about 15 mm long, corolla tube to about 22 mm long and 2.5 mm diameter at base, and 4 mm diameter at face;

Petal color: Fading slightly with maturity; upon initial opening-adaxial limb distal portion between RHS N78A and RHS NN78A, with center eye band about 3 mm wide nearest RHS NN78A toward the margin and a bar in the middle proximal face portion of nearest RHS N78A; upon initial opening — abaxial limb distal portion between RHS 77D and RHS 76C; upon initial opening abaxial corolla tube between RHS N77B and RHS N79D; upon initially opening adaxial corolla tube nearest RHS N77B in the distal two-thirds and the proximal one-third nearest RHS 145D; at maturity — adaxial limb distal portion between RHS N78A and RHS NN78A, with center eye band about 3 mm wide nearest RHS NN78A toward the margin and a bar in the middle proximal face portion of nearest RHS N81A; at maturity — abaxial limb nearest RHS N81D; at maturity abaxial corolla tube nearest RHS N79B; at maturity adaxial corolla tube distal two-thirds nearest RHS 79D and proximal one-third nearest RHS 155D;

Androecium: Five;

*Filaments.*—Typically, five; straight; cylindrical; adnate to adaxial corolla tube except free in distal 1 to 2 mm; varying lengths between 17 mm and 25 mm, about 0.2 mm in diameter; color between RHS N155B and RHS NN155D in distal free portion and the same color as the adaxial corolla proximally.

*Anther*.—Five; oblong elliptic; dorsifixed; longitudinal; about 3 mm long by 1 mm wide; color nearest RHS 11C.

*Pollen*.—Abundant; color nearest RHS 11D.

Gynoecium: One pistil per flower; to about 21 mm long;

*Style*.—Cylindrical; straight; about 18 mm long and about 0.3 mm diameter; persistent after flower abscission; color nearest RHS 145D distally and proximally with the center lightly blushed with nearest RHS N77D, transitioning to nearest RHS N186C after flower abscission.

*Stigma*.—Trifid in the distal 1 mm, about 0.3 mm in diameter; color nearest RHS 145D.

*Ovary*.—Superior; conical; acute apex, base truncate; about 2 mm long and 1 mm diameter; color nearest RHS 143A.

Calyx: Tubular; adpressed to corolla tube; to about 12 mm long and 4 mm cross at apex;

Sepals: Five; linear; narrowly acute apex, margin entire; basal 3 mm fused; adaxial surface glabrous and slightly lustrous, abaxial glabrous and slightly lustrous; persistent; individually about 9 mm long and 2 mm wide at fusion;

Sepal color: Adaxial nearest RHS 137C in center with translucent margins of nearest RHS 157D; abaxial nearest RHS 137C in center, with and midrib of nearest RHS N186C where exposed to high light, and translucent margins of nearest RHS 157D;

Peduncle: Glabrous, stiff, strong, moderately lustrous, upright, cylindrical; flowering portion average about 20 cm long, and 5 mm diameter at base of flower branches; branches to about 12 mm long and 2 mm diameter at base;

Peduncle color: RHS 146C;

Bracts: Subtending individual flowers; lanceolate; micro-ciliolate margin; acute apex; sessile truncate base; glabrous; to about 8 mm long and 2.5 mm wide;

Bract color: Same as leaves in both adaxial and abaxial surfaces;

Pedicel: Cylindrical; micro-puberulent; to about 6 mm long and 1 mm diameter;

Pedicel color: Nearest RHS 146C;

Fruit and seeds: Not yet observed;

Hardiness and culture: The new plant grows best with plenty of moisture and adequate drainage; hardy to at least from USDA zone 4 through 8.

Disease and pest resistance: *Phlox* 'Material Girl' demonstrated the excellent powdery mildew resistance caused by *Erysiphe cichoracearum* in the presence and under conditions of intense pressure that would normally show symptoms.

I claim:

1. A new and distinct cultivar of hybrid *Phlox* plant named 'Material Girl', as herein described and illustrated.

* * * * *